(12) United States Patent
Murtonen

(10) Patent No.: US 8,670,823 B2
(45) Date of Patent: Mar. 11, 2014

(54) IMPLANTABLE MEDICAL DEVICE HAVING AN MRI SAFE RECHARGEABLE BATTERY

(75) Inventor: Salomo Murtonen, Pasedena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/451,244

(22) Filed: Apr. 19, 2012

(65) Prior Publication Data
US 2012/0290022 A1 Nov. 15, 2012

Related U.S. Application Data

(60) Provisional application No. 61/484,489, filed on May 10, 2011.

(51) Int. Cl.
*A61N 1/00* (2006.01)
(52) U.S. Cl.
USPC ............................................. 607/2
(58) Field of Classification Search
USPC ..................................... 607/2, 57; 320/108
See application file for complete search history.

(56) References Cited

U.S. PATENT DOCUMENTS

| | | | |
|---|---|---|---|
| 6,067,474 A * | 5/2000 | Schulman et al. | 607/57 |
| 6,553,263 B1 | 4/2003 | Meadows et al. | |
| 7,295,878 B1 | 11/2007 | Meadows et al. | |
| 2010/0036458 A1 | 2/2010 | Duftner et al. | |
| 2011/0159371 A1 * | 6/2011 | Lyden et al. | 429/231.95 |
| 2012/0274271 A1 * | 11/2012 | Thompson et al. | 320/108 |

FOREIGN PATENT DOCUMENTS

| | | |
|---|---|---|
| EP | 2234188 | 9/2010 |
| GB | 2470577 | 12/2010 |

OTHER PUBLICATIONS

International Search Report and Written Opinion regarding corresponding PCT application No. PCT/US2012/034613, dated Jun. 4, 2012.
Lithium-ion Battery, http://en.wikipedia.org/wiki/Lithium_ion_battery (downloaded Apr. 19, 2012).

* cited by examiner

*Primary Examiner* — Niketa Patel
*Assistant Examiner* — Robert N Wieland
(74) *Attorney, Agent, or Firm* — Wong, Cabello, Lutsch, Rutherford & Brucculeri, LLP.

(57) ABSTRACT

Disclosed are improved rechargeable battery designs for an implantable medical device. The improved rechargeable battery is designed to reduce eddy currents in the conductive anode and/or cathode plates within the battery housing, thereby reducing excessive heat and vibrations caused when the battery is placed in a high magnetic field, such as within a MRI machine. Discontinuities may be cut in the anode and/or cathode plates to increase their resistance to eddy currents, while not significantly affecting the internal resistance between these plates.

18 Claims, 11 Drawing Sheets

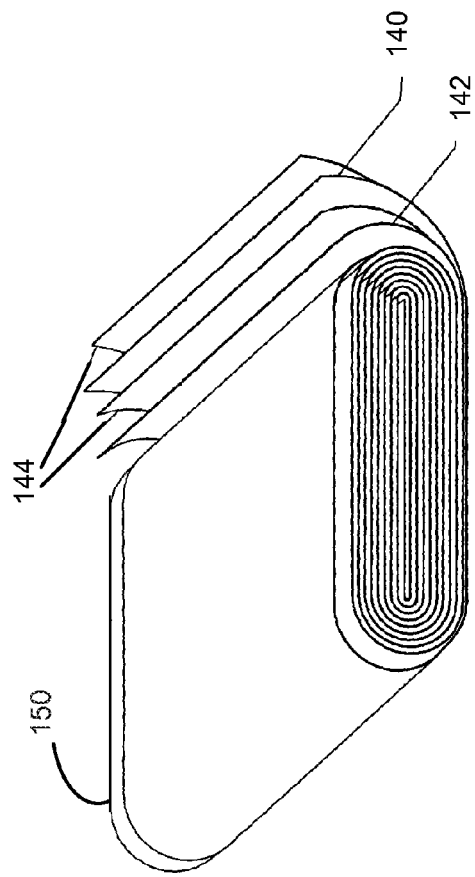
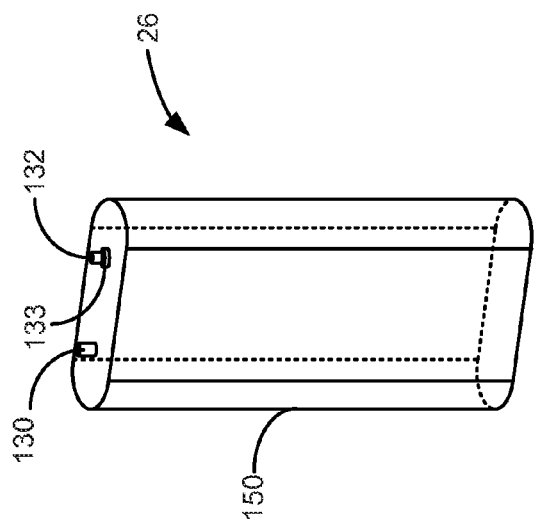
*Figure 3B (prior art)*
*Figure 3A (prior art)*

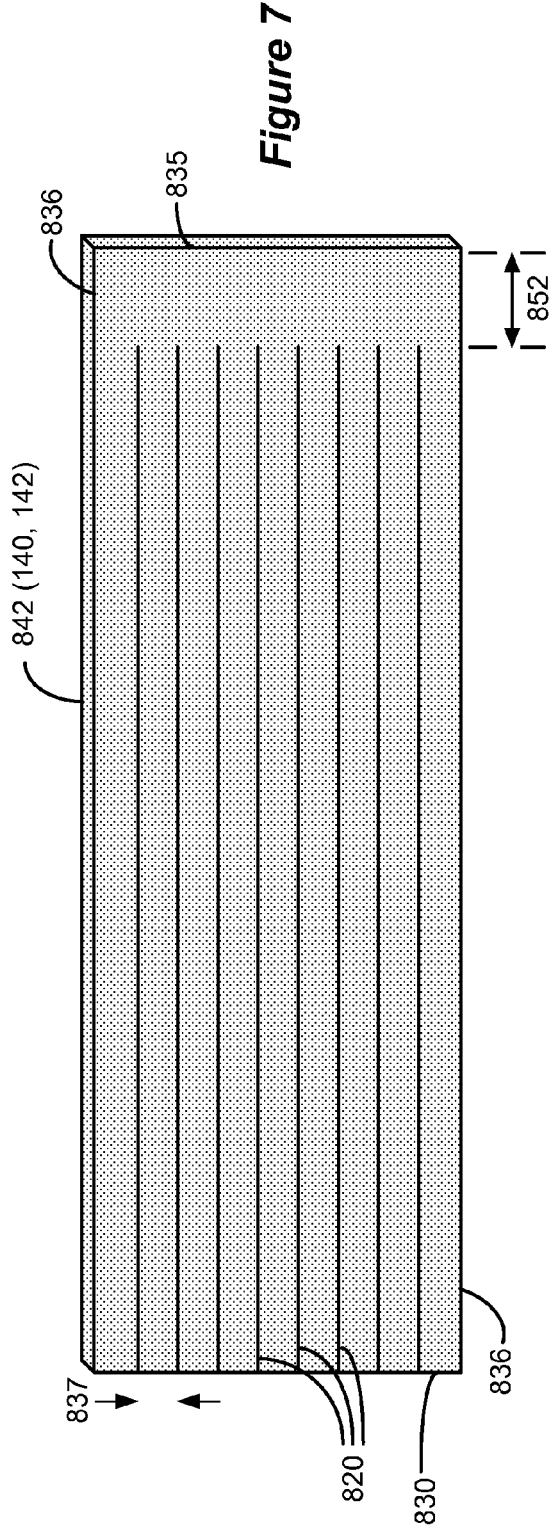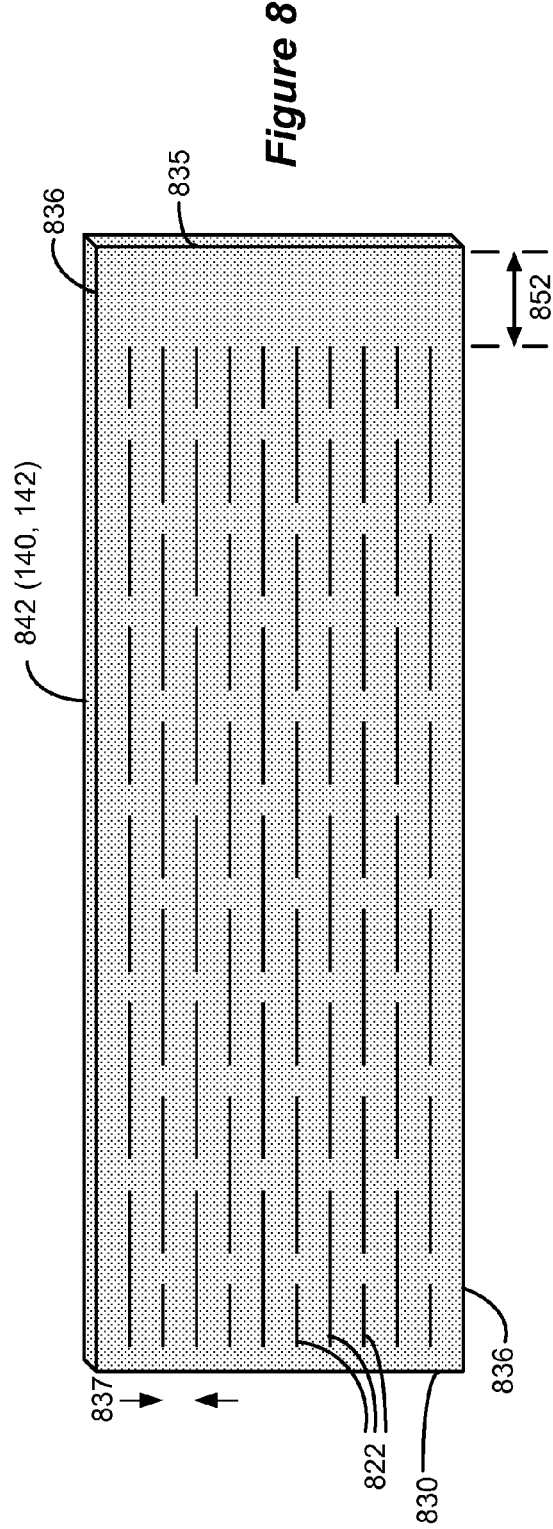

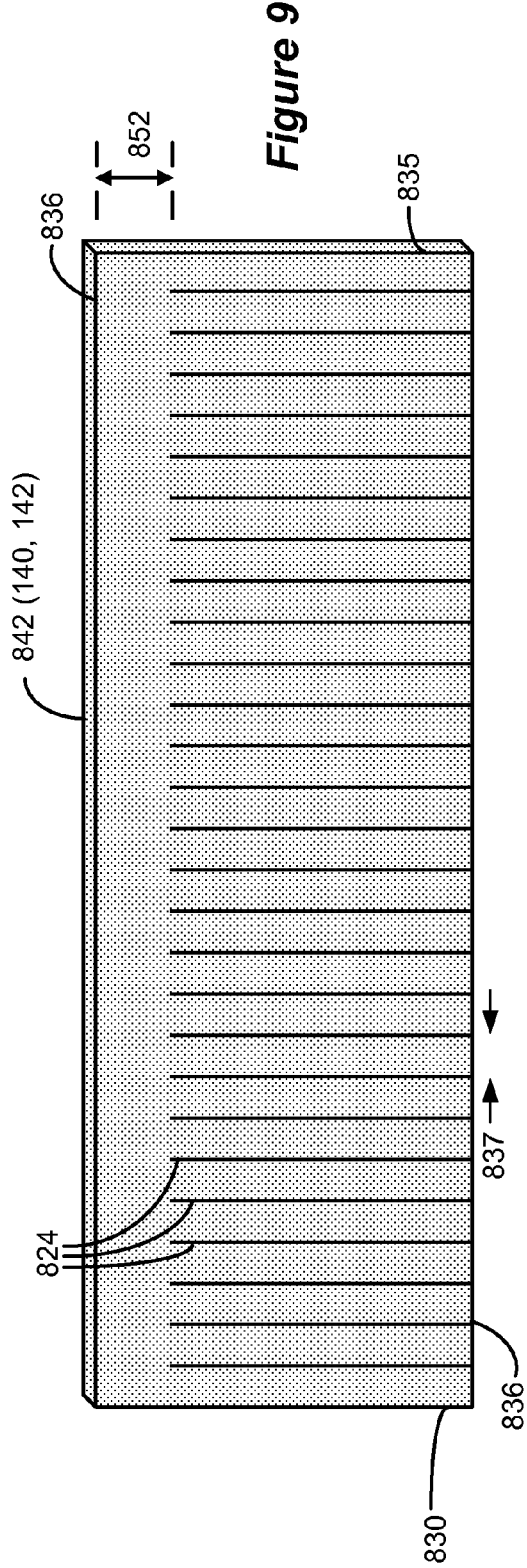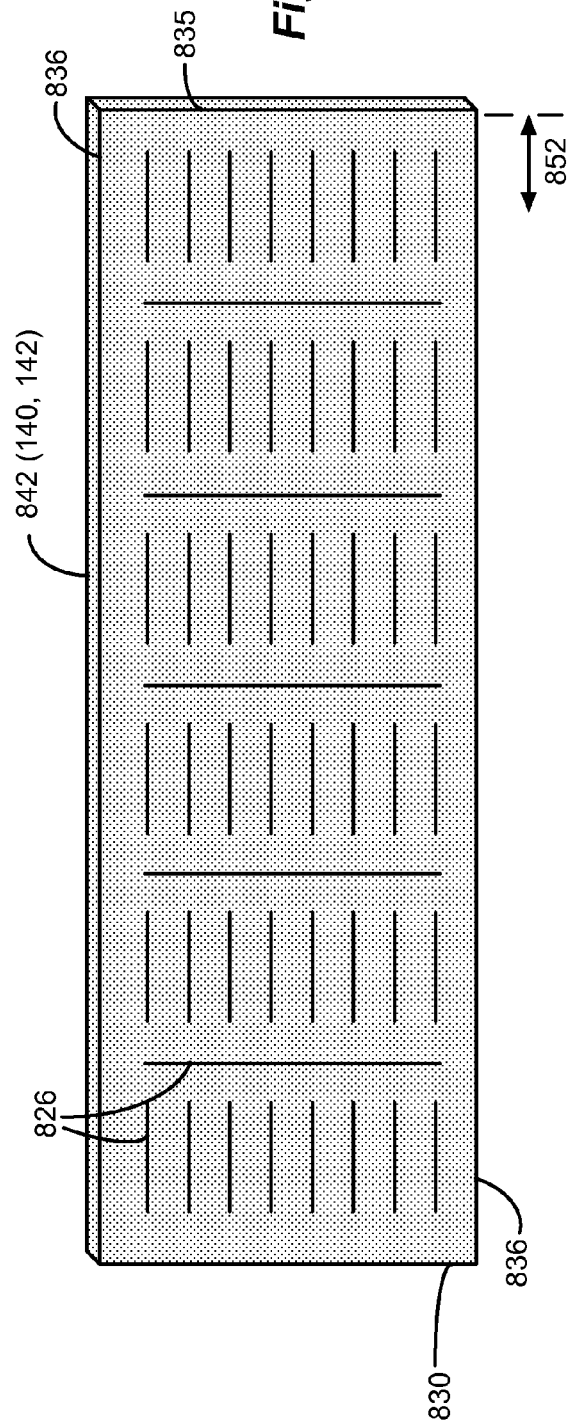

IMPLANTABLE MEDICAL DEVICE HAVING AN MRI SAFE RECHARGEABLE BATTERY

CROSS-REFERENCE TO RELATED APPLICATIONS

This is a non-provisional filing of Provisional U.S. Patent Application 61/484,489, filed May 10, 2011, to which priority is claimed in which is incorporated herein by reference in its entirety.

FIELD OF THE INVENTION

The present invention relates to an improved rechargeable battery for an implantable medical device, and an improved implantable medical device incorporating such a battery.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227, which is incorporated herein by reference in its entirety.

As shown in FIGS. 1A and 1B, a SCS system typically includes an Implantable Pulse Generator (IPG) 100, which includes a biocompatible device case 30 formed of titanium for example. The case 30 typically holds the circuitry and battery 26 necessary for the IPG to function. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102 and 104 couple to the IPG 100 using lead connectors 38a and 38b, which are fixed in a header material 36.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12; and a charging coil 18 for charging or recharging the IPG's battery 26 using an external charger 50. The telemetry coil 13 can be mounted within the header 36 of the IPG 100 as shown.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via inductive coupling. To implement such functionality, both the IPG 100 and the external controller 12 have coils 13 and 17 respectively. Either coil can act as the transmitter or the receiver, thus allowing for two-way communication between the two devices. When data is to be sent from the external controller 12 to the IPG 100 for example, coil 17 is energized with alternating current (AC), which generates a magnetic field 29, which in turn induces a voltage in the IPG's telemetry coil 13. The generated magnetic field 29 is typically modulated using a communication protocol, such as a Frequency Shift Keying (FSK) protocol, which is well known in the art. The power used to energize the coil 17 can come from a battery 76, which like the IPG's battery 26 is preferably rechargeable, but power may also come from plugging the external controller 12 into a wall outlet plug (not shown), etc. The induced voltage in coil 13 can then be demodulated at the IPG 100 back into the telemetered data signals. To improve the magnetic flux density, and hence the efficiency of the data transfer, the IPG's telemetry coil 13 may be wrapped around a ferrite core 13'.

The external charger 50 is used to charge (or recharge) the IPG's battery 26. Specifically, and similarly to the external controller, the coil 17' is energized with an AC current to create a magnetic field 29. This magnetic field 29 induces a current in the charging coil 18 within the IPG 100, which current is rectified to DC levels, and used to recharge the battery 26. The external charger 50 will generally have many of the same components as the external controller 12, and therefore have similar element numerals, denoted with prime symbols. However, while sufficient for purposes of this disclosure to view the external controller 12 and charger 50 as essentially the same, one skilled in the art will realize that external controllers 12 and chargers 50 will have pertinent differences as dictated by their respective functions.

As is well known, inductive transmission of data or power can occur transcutaneously, i.e., through the patient's tissue 25, making it particularly useful in a medical implantable device system. During the transmission of data or power, the coils 13 and 17, or 18 and 17', preferably lie along a common axis in planes that are parallel. Such an orientation between the coils will generally improve the coupling between them, but deviation from ideal orientations can still result in suitably reliable data or power transfer.

A rechargeable battery 26 for the illustrated IPG 100 is shown in FIGS. 3A and 3B, which depicts an exemplary 3.6V, 200 mAh lithium ion battery, part number QL02001-A, manufactured by Quallion, LLC. As shown, the battery 26 is generally in the shape of a "squashed" cylinder. The battery 26 includes an external housing 150; its internal components can be seen in cross section in FIG. 3B. Specifically noticeable are four plates that have been spirally wound within the housing 150: a conductive anode plate 140, a conductive cathode plate 142, and two separator plates 144. An electrolyte (not shown) fills the spaces between the various plates, as is well known.

FIG. 4 shows the anode plate 140, the cathode plate 142, and the separator plates 144 unrolled as separate sheets for simplicity. The anode plate 140 includes anodic materials such as graphite for example. The anode plate 140 can also include a substrate upon which the anodic material is placed, such as a titanium substrate. However, the delineation of such layers in the anode plate 140 is not shown in FIG. 4 for simplicity. The cathode plate 142 includes Lithium-based cathodic materials such as $LiC_6$, $Li_4Ti_5O_{12}$, $LiCoO_2$, or $LiNiCoO_2$ for example. Again, the cathode plate 142 can include a substrate upon which the cathodic materials are placed, such as aluminum. The separator plates 144 can comprise many materials, such as polyethylene. Other details concerning lithium ion batteries and their materials can be found at U.S. Pat. No. 6,553,263 and also at http://en.wikipedia.org/wiki/Lithium_ion_battery, a copy of which is included in the Information Disclosure Statement filed herewith, both of which are incorporated herein by reference in their entireties.

As is typical, the anode plate 140 and cathode plate 142 are coupled to two external battery terminals 132 and 130, respectively, as shown in FIGS. 3A and 4. The cathode battery terminal 130 is coupled to the battery case 150, while the anode battery terminal 132 is insulated from the battery case by an insulator 133 (FIG. 3A). Whether the battery housing 150 is coupled to the anode or cathode depends on the design, and can vary. The battery terminals 130 and 132 are ultimately electrically connected to the PCB 16 (FIG. 2) in the IPG 100, such as by soldering.

The inventor has noticed that an implantable medical device having a rechargeable lithium ion battery such as the battery 26 may interfere with a patient's use of magnetic resonance imaging (MRI). In particular, the inventor is concerned that when an MRI operation is being performed on a patient with an implantable device such as IPG 100, the MRI's magnetic fields may interfere with the battery 26. As a result of such interference, the battery 26 may become excessively hot and may even vibrate.

FIG. 5 shows a cross section of an MRI machine 500 with a patient 545 inside. The MRI machine 500 includes a static magnet 502 and three gradient magnets 504, 506 and 508. The three gradient magnets 504, 506 and 508 are each aligned in X, Y and Z planes respectively. Gradient magnets 504, 506 and 508 generate an alternating X magnetic field 520, an alternating Y magnetic field 530, and an alternating Z magnetic field 540 respectively. The static magnet 502 generates a static magnetic field 550 of 0.5-tesla to 3.0-tesla or more, or 5,000 to 30,000 gauss or more, which is a very strong magnetic field.

When a patient having an IPG 100 with a battery 26 is placed inside the MRI 500 machine, the alternating magnetic fields 520, 530, and 540 of the MRI induce circulating currents in the conductive plates 140 and 142 and the housing 150 of the battery 26. These currents are known as eddy currents, and are shown generically in FIG. 6 as a current 606 responsive to one of the alternating magnetic fields 602 (e.g., 520, 530, or 540) of the machine 500. (Eddy currents 606 are only shown in a major surface of the battery 26 in FIG. 6 for convenience, but it will be understood that the plurality of alternating fields 520, 530, and 540 would cause other eddy currents in other surfaces of the battery 26). Such eddy currents 606 can heat the battery 26, which can in turn heat the IPG 100. Such heat can cause discomfort for the patient and can also result in decreased battery life.

The inventor considers the eddy currents 606 in the battery 26 problematic in another way which relates to the MRI environment. Pursuant to a principle known as Lenz's law, eddy currents 606 induce alternating magnetic field 604 which generally opposes the field 602 that created it. This induced alternating magnetic field 604 can react with the strong static magnetic field 550 in the MRI machine 500. Generally speaking, the static magnetic field 550 will have fixed north and south poles, while the induced alternating magnetic field 604 will have north and south poles that alternate. These two fields 604 and 550 will react with one another so as to place a mechanical force on the battery 26 that alternatively pushes and pulls the battery 26 along an axis with a frequency matching that of the alternating field 604. In other words, the induced alternating magnetic field 604 will cause the battery 26 to vibrate in the presence of the static magnetic field 550. The larger the magnitude of the eddy currents 606, the stronger the induced alternating magnetic field 604, and hence the stronger the vibrational force on the battery 26. Such vibrations can weaken mechanical fastenings of the battery 26 inside of the housing 30 of the IPG 100, and may result in breaking solder joints or damaging other components in the IPG 100.

Additionally, the induced alternating magnetic fields 604 generated by the eddy currents 606 in the battery 26 can cause distortions in the area around the IPG, thus negatively affecting MRI image quality.

Given the shortcomings of the rechargeable battery of the prior art, it would be beneficial to provide an improved rechargeable battery for an implantable medical device, and this disclosure presents such a solution.

BRIEF DESCRIPTION OF THE DRAWINGS

FIGS. 3A and 3B show a prior art rechargeable battery for an IPG having a spiraled anode/separator/cathode structure.

FIGS. 7-11 show different embodiments of improved designs for a conductive anode and/or cathode plate for an improved rechargeable battery having slits cut therein.

DETAILED DESCRIPTION

Figures 1A, 1B:
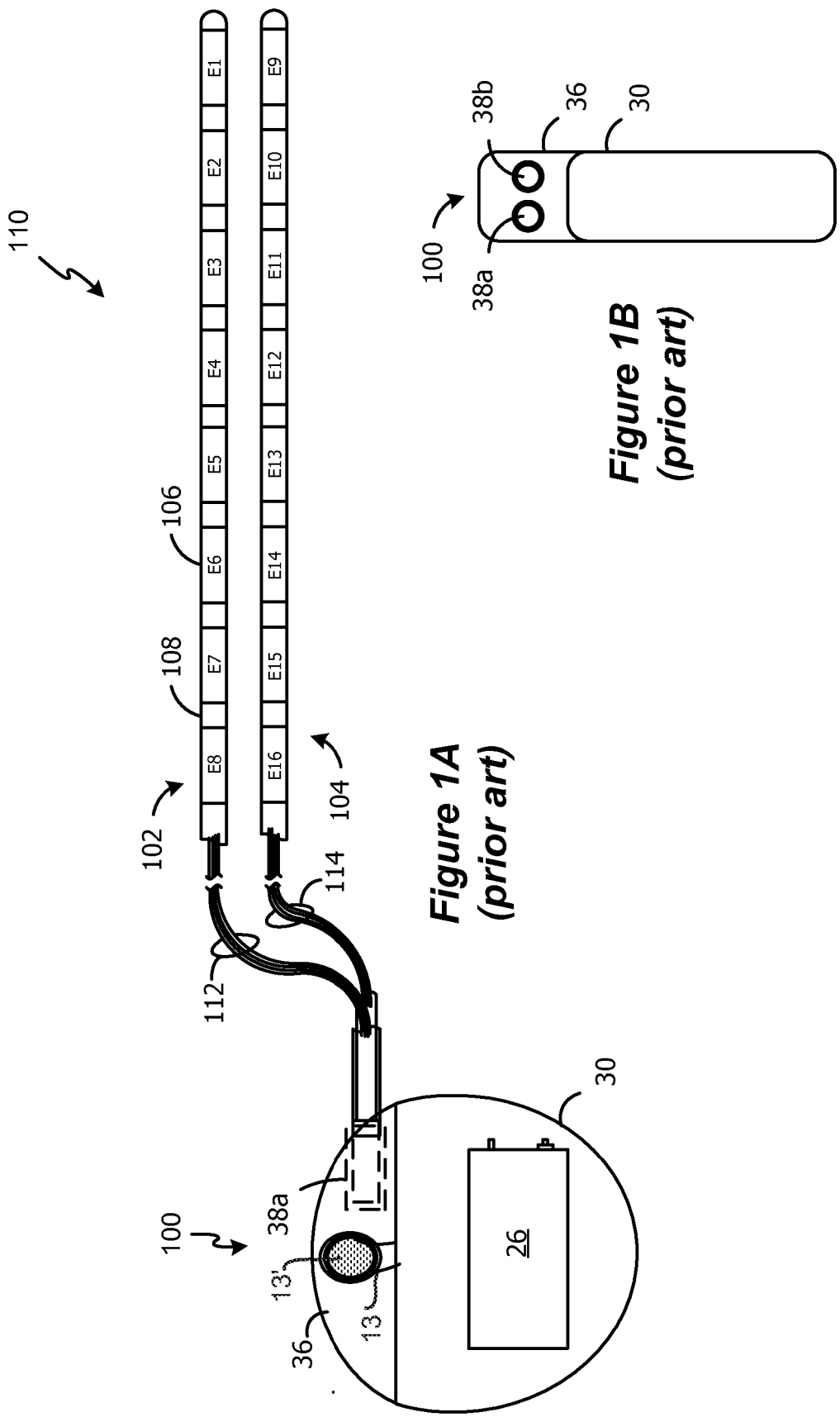
FIGS. 1A and 1B show an implantable pulse generator (IPG), and the manner in which an electrode array is coupled to the IPG in accordance with the prior art.
Figure 2:
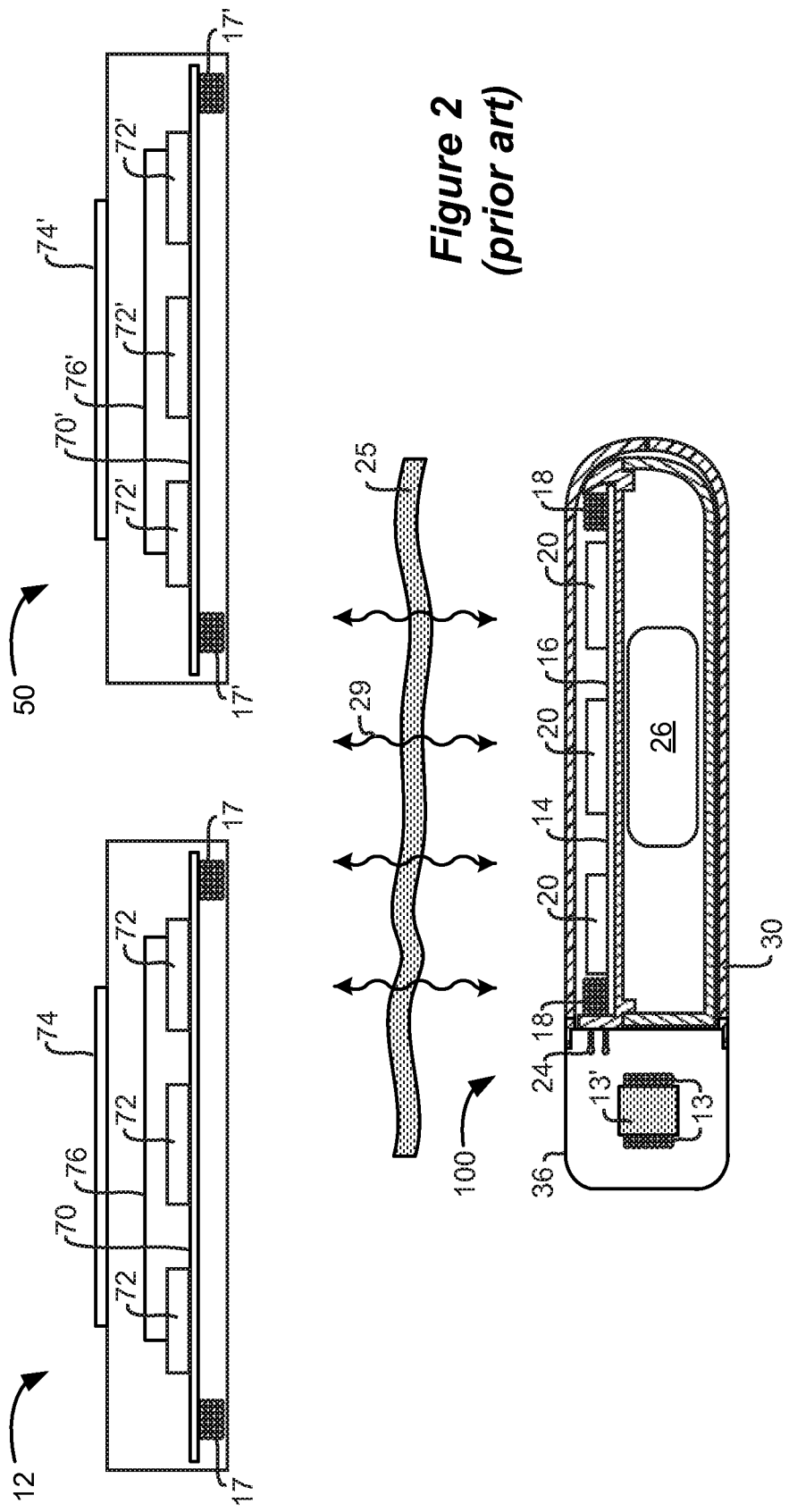
FIG. 2 shows the relation between the IPG and an external controller and an external charger.

The description that follows relates to use of the invention within a spinal cord stimulation (SCS) system. However, it is to be understood that the invention is not so limited. Rather, the invention may be used with any type of implantable medical device system that could benefit from an improved battery design. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

Disclosed are improved rechargeable battery designs for an implantable medical device. The improved rechargeable battery is designed to reduce eddy currents in the conductive plates within the battery housing, thereby reducing excessive heat and vibrations caused when the battery is placed in a high magnetic field, such as within a MRI machine.

FIG. 7 shows a first embodiment for reducing eddy currents in the conductive plates of a battery for an implantable medical device, which involves cutting a number of narrow slits 820 in the conductive plate 842 of the battery. The conductive plate 842 is representative of either or both of the anode plate 140 (FIG. 4) and cathode plate 142 of the improved battery, and can be made of the same anodic or cathodic materials discussed earlier in the Background.

The slits 820 are cut horizontally on the surface of the plate 842 parallel to its long edges 836 to break up the surface area. The slits 820 create electrical discontinuities in the surface area, which increases resistance to currents within a plane of the plate, and thus impedes the flow of eddy currents in the plate 842. In particular, the slits 820 impede the flow of current in perpendicular to the slits, i.e., vertically in FIGS. 7-8.

The slits 820 begin at a distance 852 away from a first short edge 835, but then terminate at the opposing second short edge 830. This prevents eddy currents from flowing around the slits 820 proximate to short edge 830 at least. Eddy currents could still flow around the edges of the slits 820 proximate to short edge 835, but keeping the plate 842 uncut at this location also provides some benefits. First, the uncut portion 852 provides an area of high current density, which can prevent overheating and damage to the plate 842. Second, the uncut portion 852 makes the plate 842 easier to handle during battery manufacturing, and keep the plate 842 in one piece. However, this is not strictly necessary, and instead the slits 820 could extend all the way from edge 830 to edge 835. If this occurs, tape or other adhesive could be used proximate edge 835 to keep the plate 842 essentially intact after the slits 820 are cut to ease subsequent manufacture and handling.

The number and spacing 837 of the slits 820 is subject to designer preferences, and can be dictated by the expected susceptibility of the plate 842 in question to eddy currents, which may require consideration of the conductivity of the plate 842, the frequency of the perturbing magnetic field 602 (FIG. 6), and other factors. The larger the number of slits 820 and the smaller their spacing 837, the more effective the battery will be at reducing the adverse effects of eddy currents mentioned previously. However, a larger number of slits and smaller spacing may make the plate 842 difficult to handle during manufacturing. Moreover, a large number of slits or tight spacing will eventually start to effectively reduce the surface area of the plate 842, which would increase the internal resistance of the battery. Experimentation or simulation may assist in setting the number of spacing of the slits.

Notice that while the slits 820 impede the flow of current within the plane of the plate 842, the surface area of the plate otherwise remains unchanged. As such, battery performance—i.e. the flow of ions within the battery from the cathode to the anode plate—is not significantly affected. That is, battery current perpendicular to the plane of the plate 842 is not significantly affected by the slits 820.

The slits 820 can be formed by placing an otherwise completed plate 842 under a multi-blade device (not shown) and then pressing the multi-blade device down on the plate to create multiple narrow slits. Both the anode 140 and cathode 142 plates could be cut simultaneously, or each plate could be cut individually and separately. In yet another embodiment, the second plate is positioned under the blade such that the slits are offset by a small distance from the slits that were cut in the first plate. The slits 820 may also not be cut all of the way through the plate 842, but may instead merely indent or score the plates, which would also increase resistance to currents within the plane of the plates.

Figure 4:
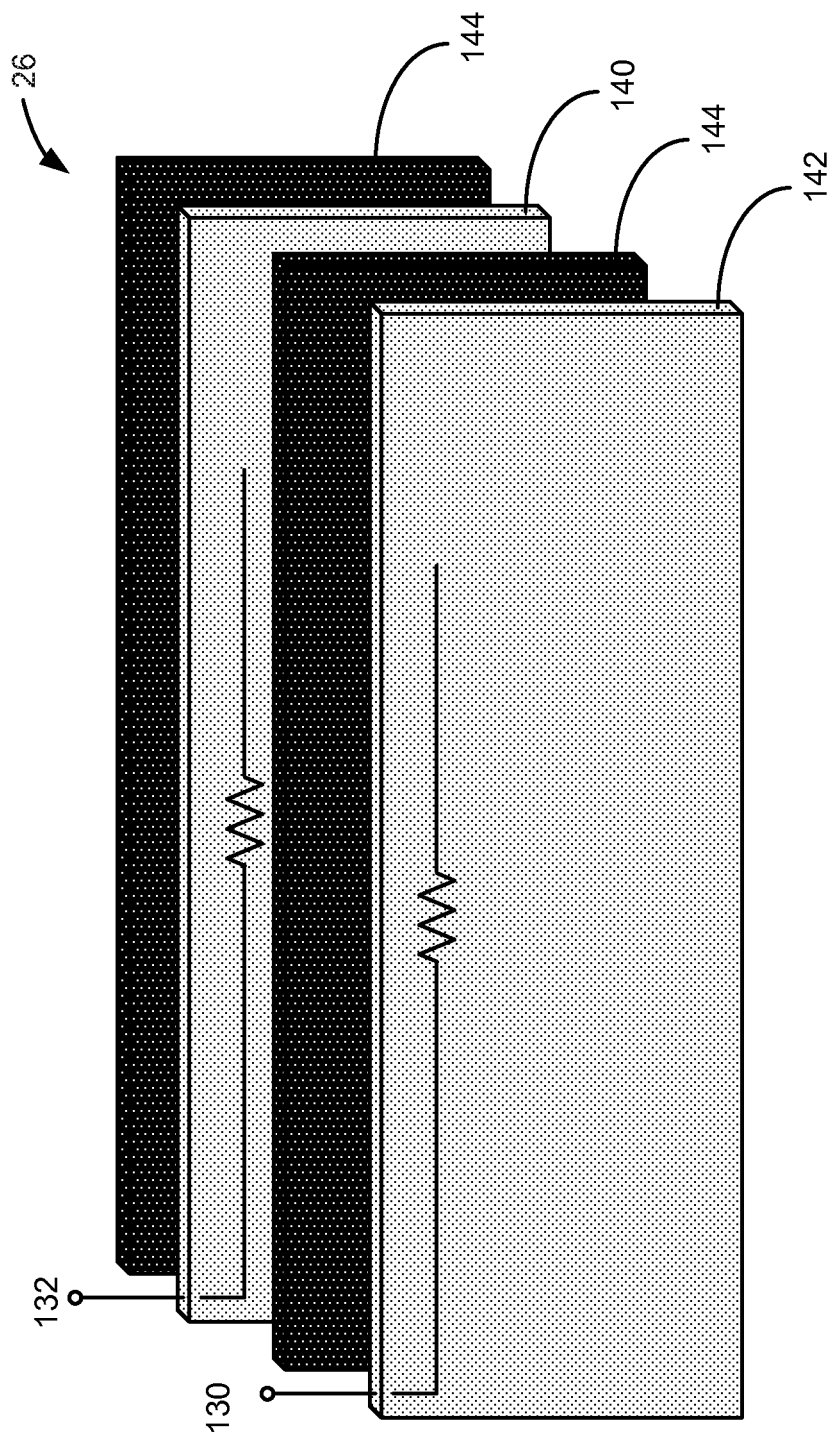
FIG. 4 shows unrolled plates of the prior art battery of FIG. 3 for simplicity.
Figure 5:
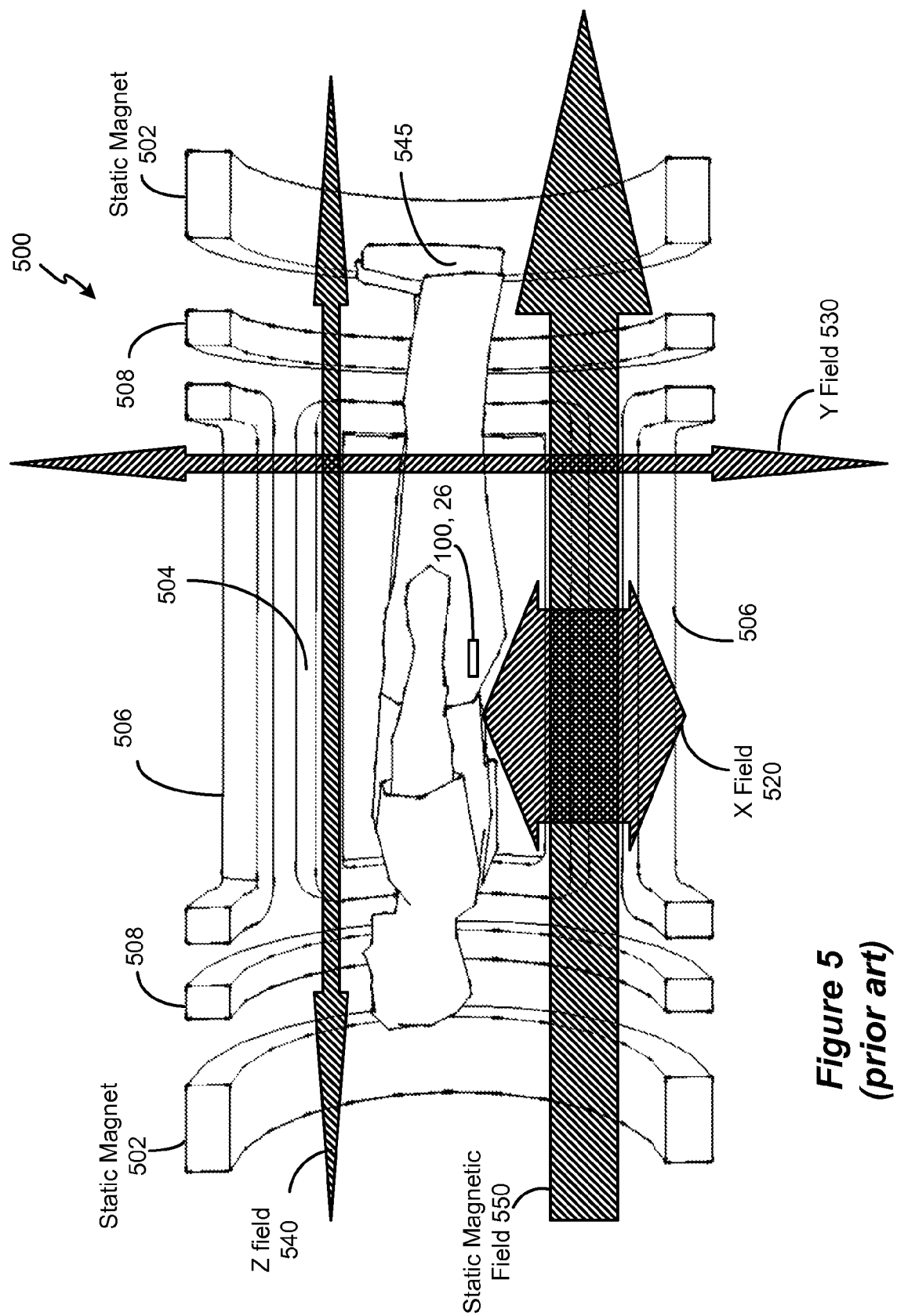
FIG. 5 shows the structure of magnets in an MRI and their position with respect to a patient placed inside the MRI machine.

Once the plates 842 have been cut, the battery 26 can be fabricated using traditional fabrication steps. Assuming both the anode plate 140 and the cathode plate 142 have been cut, the cut anode plate 140 is placed in between two separator plates 144 (FIGS. 3B and 4). The cut cathode plate 142 is then placed on top of the second separator 144, and the resulting structure is then folded (e.g., rolled) into a configuration (e.g., a spiral configuration), such as shown in FIG. 3B. The configuration is placed inside a battery housing 150 that is conformal in shape to the battery 26 (FIGS. 3A-3B). The anode 140 and cathode 142 plates are then coupled to two external battery terminals 132 and 130 (FIGS. 3A and 4). One of those battery terminals is then coupled to the battery housing 150, and the housing is then hermetically sealed.

Figure 11:
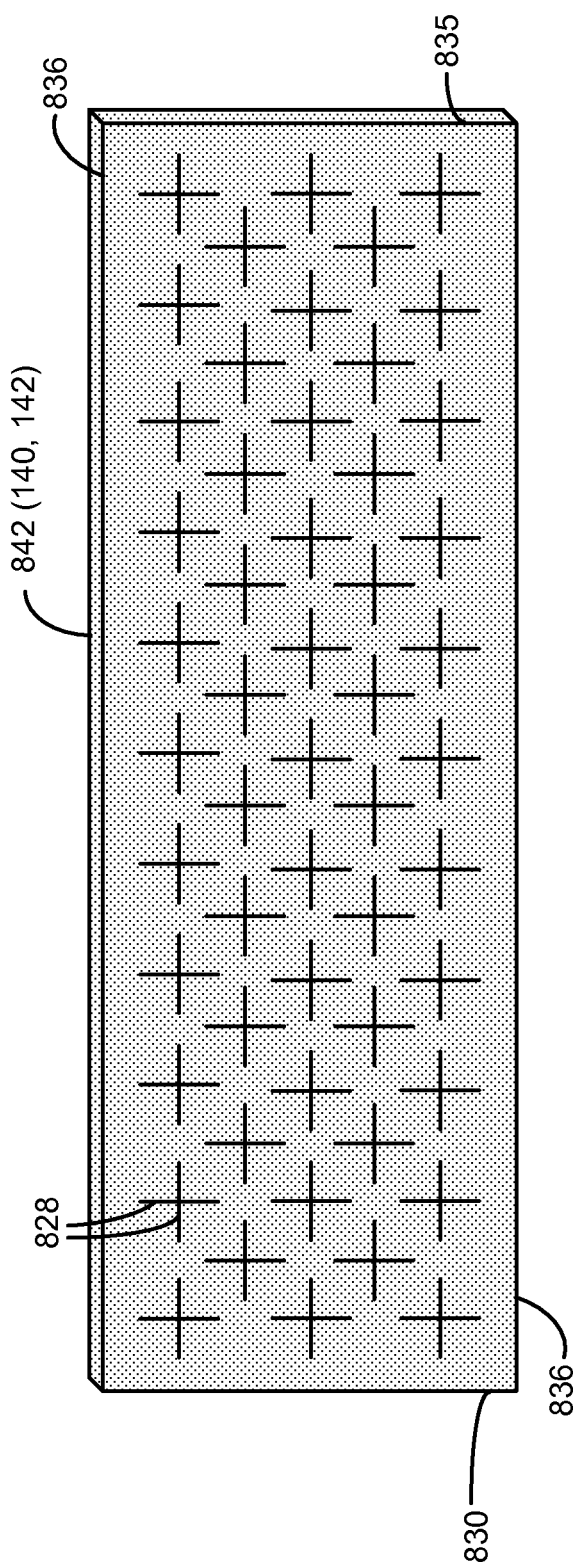

FIGS. 8-11 shows different geometries for the slits for reducing eddy currents in the conductive plates of a battery for an implantable medical device. In FIG. 8, the slits 822 in each row are formed in pieces rather than comprise a single cut between ends 830 and 835, and even and odd numbered rows are staggered. In this example, vertical current in the plate 842 is diverted around the slits, which increase resistance in this direction on the plate. In FIG. 9, the slits 824 are made parallel to the short edges 830 and 835. In FIG. 10, both vertical and horizontal slits 826 are used. In FIG. 11, the horizontal and vertical slits 828 intersect to form crosses. One skilled in the art will appreciate that in each of these examples, the flow of eddy currents in the plane of the plate 842 will be interrupted to various degrees as desired. Slit geometries beyond those shown are still possible.

Figure 12A:
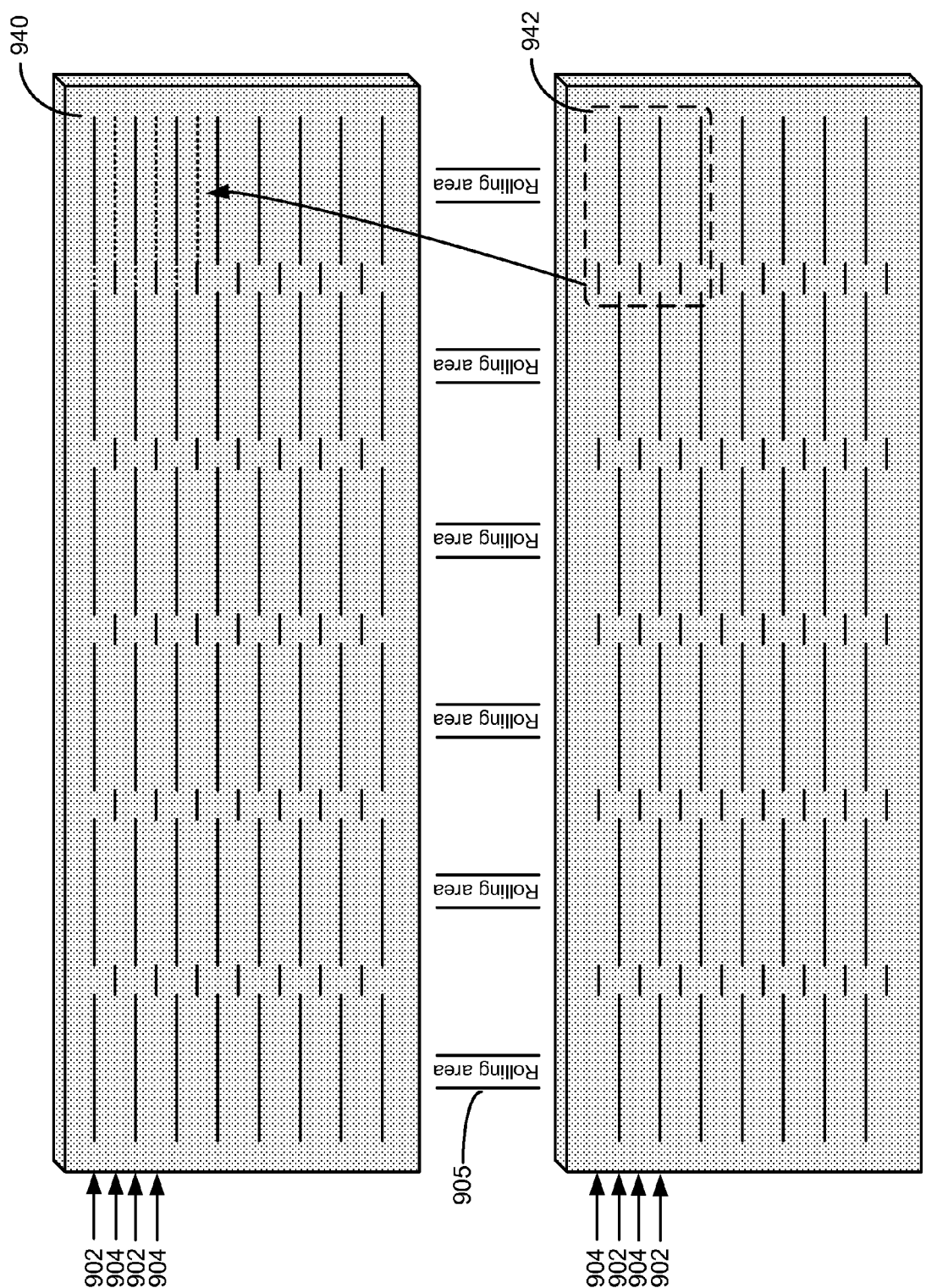
FIGS. 12A-12C shows another embodiment in which the anode and cathode plates have complementary slits formed therein.

FIG. 12A shows yet another embodiment, and shows that slits can be made differently but complementary on the anode plate 940 and the cathode plate 942. Both the anode and cathode plates 940 and 942 are cut with alternating rows 902 of long slits and rows 904 of short slits. However, the rows are offset between the two plates 940 and 942, such that the anode plate 940 starts with a row 902 of long slits, while the cathode plate 942 starts with a row 904 of short slits. This arrangement renders the slits on the plates complementary: when these plates are overlaid, as they would be when wound together to form a completed battery, the gaps in the rows in one plate are filled by slits from the other plate. A portion of such overlay is shown to the right in FIG. 12A, which specifically shows the relative position of some of the cathode plate slits on the anode plate in dotted lines. The benefit of such complementary slits will be discussed shortly.

Also shown in FIG. 12A are rolling areas 905 where the anode and cathode plates 940 and 942 would be bent as they are rolled together to form the finished battery as discussed earlier. As shown, the rolling areas correspond to the position of the long slits in the two plates 940 and 942. Although not shown for convenience, the long slit portions would gradually increase in length to accommodate the increase of size in the resulting structures as it is rolled. For example, if the left edge as shown in FIG. 12A will comprise the inner-most portion of the rolled structure, then the long slits would be relatively short at this end and would steadily grow toward the right edge of the plates. The resulting rolled structure is shown in FIG. 12B.

Figure 6:
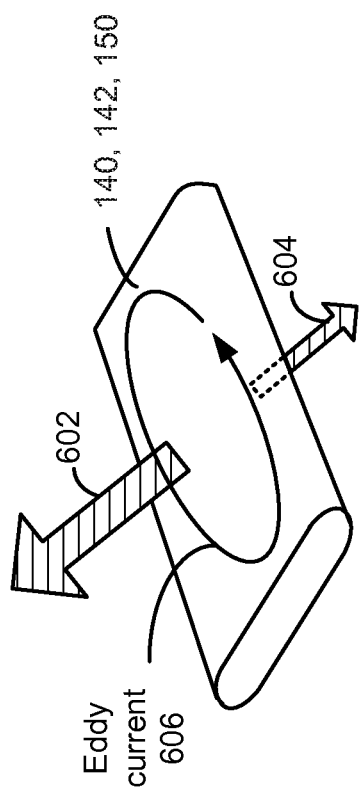
FIG. 6 shows the effects of an alternating magnetic field in producing eddy currents in a prior art rechargeable battery.
Figure 12C:
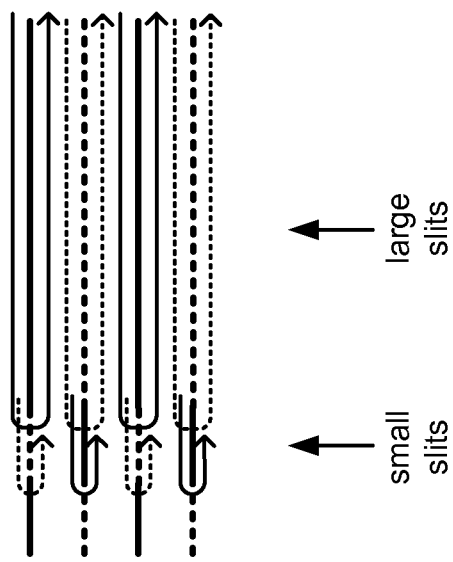

The complementary nature of the slits in the anode and cathode plates 940 and 942 do not permit eddy currents to flow in the same locations in the two plates. This is because an open path around the slits in one plate would be blocked by the slits in the other plate. Such different positioning of eddy currents in the two plates 940 and 942 is shown in FIG. 12C, which shows only a small part of the plates and just few slits. In this example, slits in the anode plate 940 and cathode plate 942 are shown as overlaid as they would be in a battery, with the anode plate 940 slits being drawn in solid lines and the cathode plate 942 slits in dotted lines. Also shown are eddy currents flowing around the various slits, again either in solid or dotted lines depending on whether they occur in the anode or cathode plates. As can be seen, the eddy currents appear in different locations in each of the plates, but all travel in the same counterclockwise direction in this example in reaction to the particular perturbing alternating magnetic field at issue (602; FIG. 6). When one consider a particular overlaid location, the eddy currents in one of the plates tends to be met with a current from the other plate that is traveling in the opposite direction. As such, offsetting the location of the eddy currents in the plates 940 and 942 in this way tends to cancel out their effects. Therefore, these eddy currents will produce a smaller effective induced alternating magnetic fields (604; FIG. 6) and as such will not react as strongly to a high static magnetic field, such as occurs in an MRI machine 500 as noted earlier.

Figure 12B:
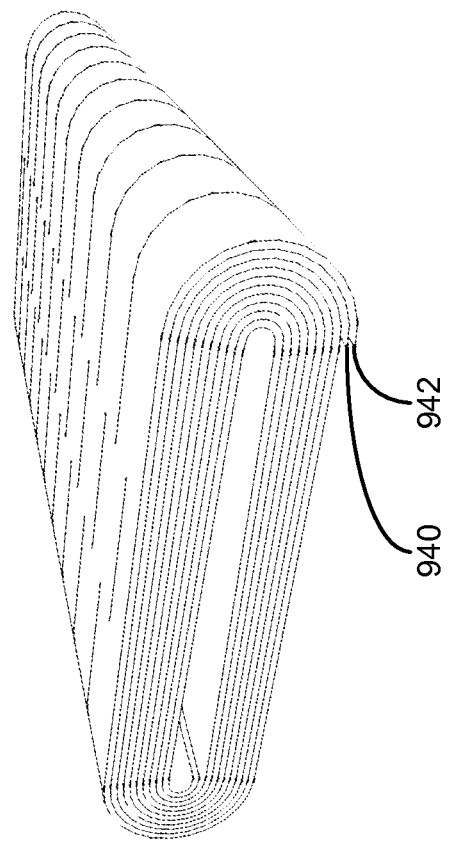

Although the use of long and short slits have been shown in FIGS. 12A and 12B, it should be understood that the complementary slits could also all be of the same length, and that the slits need not appear in pre-designed rolling areas 905. Additionally, complementary slits in the two plates 940 and 942 can be formed in other ways. For example, the slits in one of the plates could be translated in both horizontal and vertical directions from their locations in the other plate.

As mentioned earlier, eddy currents can also be formed in the battery housing 150 (FIG. 1), as well as in the conductive plates that comprise anode and the cathode. Because the battery housing 150 is normally hermetic in an implantable medical device, use of the sorts of slits disclosed herein to provide additional eddy current resistance may not be advisable. Having said this, the battery housing 150 could be formed with slits as disclosed herein if additional steps are taken to ensure good hermiticity, such as by coating the housing once the slits are formed.

The battery housing 150 may also combat eddy currents by the use of high electrical resistance materials, such as amorphous metals. An amorphous metal is a metallic material with a disordered atomic-scale structure. Amorphous metals are normally alloys rather than pure metals. In contrast to most metals which are crystalline and therefore have a highly ordered arrangement of atoms, amorphous alloys are non-crystalline. Examples of amorphous metals that can be used in the battery housing 150 include the alloys of boron, silicon, phosphorus, and other glass formers with magnetic metals (iron, cobalt, nickel). By making the battery housing 150 from such materials, the amount of eddy currents generated in the housing is reduced, thereby limiting heating and vibration of the battery.

Although the embodiments of the improve battery design disclosed herein have to this point involved the use of slits in the anode and/or cathode plates to reduce the effects of eddy currents, it should be understood that structures other than slits can be used to form the desired discontinuities. For example, holes or slots could also be used. However, to the extent forming a discontinuity removes surface area from the anode or cathode plates, such removal will increase the internal resistance of the resulting battery, which may or may not be acceptable n a given application.

Although the embodiments described herein relate to rechargeable battery designs, the present invention is not limited to use in such batteries. Embodiments of the present invention can also be utilized in primary batteries, capacitors, super capacitors and any other device having foil electrodes. Moreover, embodiments of the present invention can be implemented not only in coiled batteries or capacitors, but also in batteries having layer stack electrodes. Finally, while the disclosed battery was developed in light of the particular problem of safe and reliable operation in an MRI environment, the disclosed battery design is not limited to that environment.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A rechargeable battery, comprising:
    an anode plate coupled to an anode terminal of the battery, wherein the anode plate has a first surface area defined by long edges and short edges of the anode plate; and
    a cathode plate coupled to a cathode terminal of the battery, wherein the cathode plate has a second surface area defined by long edges and short edges of the cathode plate,
    wherein either or both of the anode plate and the cathode plate comprise one or more slits to increase resistance to currents within a plane of the plate,
    wherein the one or more slits do not remove surface area from the first or second surface areas of either or both of the anode or cathode plates,
    wherein the slits form one or more rows of parallel slits in the anode or cathode plate on which they are located, and
    wherein odd and even numbered rows are staggered.

2. The rechargeable battery of claim 1, wherein each of the slits are parallel to the long edges of the anode or cathode plate on which they are located.

3. The rechargeable battery of claim 1, wherein each of the slits are parallel to the short edges of the anode or cathode plate on which they are located.

4. The rechargeable battery of claim 1, wherein the anode plate comprises a first substrate with an anodic material, and wherein the cathode plate comprises a second substrate with a cathodic material.

5. The rechargeable battery of claim 1, wherein the one or more slits do not proceed all of the way through either or both of the anode plate and the cathode plate comprising the one or more slits.

6. An implantable medical device, comprising:
    a rechargeable battery, comprising:
        an anode plate coupled to an anode terminal of the battery, wherein the anode plate has a first surface area defined by long edges and short edges of the anode plate; and
        a cathode plate coupled to a cathode terminal of the battery, wherein the cathode plate has a second surface area defined by long edges and short edges of the cathode plate,
        wherein either or both of the anode plate and the cathode plate comprise one or more slits to increase resistance to currents within a plane of the plate,
        wherein the one or more slits do not remove surface area from the first or second surface areas of either or both of the anode or cathode plates,
        wherein the slits form one or more rows of parallel slits in the anode or cathode plate on which they are located, and
        wherein odd and even numbered rows are staggered.

7. The implantable medical device of claim 6, wherein each of the slits are parallel to the long edges of the anode or cathode plate on which they are located.

8. The implantable medical device of claim 6, wherein each of the slits are parallel to the short edges of the anode or cathode plate on which they are located.

9. The implantable medical device of claim 6, wherein the anode plate comprises a first substrate with an anodic material, and wherein the cathode plate comprises a second substrate with a cathodic material.

10. The implantable medical device of claim 6, wherein the one or more slits do not proceed all of the way through either or both of the anode plate and the cathode plate comprising the one or more slits.

11. A rechargeable battery, comprising:
an anode plate coupled to an anode terminal of the battery, wherein the anode plate has a first surface area defined by long edges and short edges of the anode plate; and
a cathode plate coupled to a cathode terminal of the battery, wherein the cathode plate has a second surface area defined by long edges and short edges of the cathode plate,
wherein either or both of the anode plate and the cathode plate comprise one or more slits to increase resistance to currents within a plane of the plate,
wherein the one or more slits do not remove surface area from the first or second surface areas of either or both of the anode or cathode plates, and
wherein one or more slits are parallel to the short edges and one or more slits are parallel to the long edges of the anode or cathode plate on which they are located.

12. The rechargeable battery of claim 11, wherein some of the slits form one or more rows of parallel slits in the anode or cathode plate on which they are located.

13. The rechargeable battery of claim 11, wherein the anode plate comprises a first substrate with an anodic material, and wherein the cathode plate comprises a second substrate with a cathodic material.

14. The rechargeable battery of claim 11, wherein the one or more slits do not proceed all of the way through either or both of the anode plate and the cathode plate comprising the one or more slits.

15. An implantable medical device, comprising:
a rechargeable battery, comprising:
an anode plate coupled to an anode terminal of the battery, wherein the anode plate has a first surface area defined by long edges and short edges of the anode plate; and
a cathode plate coupled to a cathode terminal of the battery, wherein the cathode plate has a second surface area defined by long edges and short edges of the cathode plate,
wherein either or both of the anode plate and the cathode plate comprise one or more slits to increase resistance to currents within a plane of the plate,
wherein the one or more slits do not remove surface area from the first or second surface areas of either or both of the anode or cathode plates, and
wherein one or more slits are parallel to the short edges and one or more slits are parallel to the long edges of the anode or cathode plate on which they are located.

16. The implantable medical device of claim 15, wherein some of the slits form one or more rows of parallel slits in the anode or cathode plate on which they are located.

17. The implantable medical device of claim 15, wherein the anode plate comprises a first substrate with an anodic material, and wherein the cathode plate comprises a second substrate with a cathodic material.

18. The implantable medical device of claim 15, wherein the one or more slits do not proceed all of the way through either or both of the anode plate and the cathode plate comprising the one or more slits.

* * * * *